United States Patent [19]
Dias et al.

[11] Patent Number: 5,284,148
[45] Date of Patent: Feb. 8, 1994

[54] INTRACAVITY ULTRASOUND DIAGNOSTIC PROBE USING FIBER ACOUSTIC WAVEGUIDES

[75] Inventors: J. Fleming Dias, Palo Alto; Hewlett E. Melton, Jr., Sunnyvale, both of Calif.

[73] Assignee: Hewlett-Packard Company, Palo Alto, Calif.

[21] Appl. No.: 918,298

[22] Filed: Jul. 22, 1992

Related U.S. Application Data

[63] Continuation-in-part of Ser. No. 579,428, Sep. 7, 1990, Pat. No. 5,152,291, which is a continuation-in-part of Ser. No. 352,517, May 16, 1989, Pat. No. 5,217,018.

[51] Int. Cl.$^5$ ............................................. A61B 8/12
[52] U.S. Cl. ........................... 128/662.06; 128/661.08; 128/663.01
[58] Field of Search .................. 128/662.06, 663.01, 128/662.03, 661.08, 660.09; 73/861.25

[56] References Cited

U.S. PATENT DOCUMENTS

| | | | |
|---|---|---|---|
| 4,532,933 | 8/1985 | Hokanson | 128/663.01 |
| 4,794,931 | 1/1989 | Yock | 128/660.03 |
| 5,000,185 | 3/1991 | Yock | 128/662.03 |
| 5,054,492 | 10/1991 | Scribner et al. | 128/662.06 |
| 5,078,149 | 1/1992 | Katsumata et al. | 128/663.01 |
| 5,152,291 | 10/1992 | Dias | 128/662.06 |
| 5,170,793 | 12/1992 | Takano et al. | 128/663.01 |

OTHER PUBLICATIONS

N. Bom, et al, *Early and Present Examples of Intraluminal Ultrasonic Echography*, SPIE V. 1068 Catheter-Based Sensing and Imaging Technology, 1989, pp. 146-150.

C. K. Jen, et al, *Newly Developed Cladded Acoustic Rods*, 1991 IEEE Ultrasonic Simposium, pp. 885-890.

C. K. Jen, *Acoustic Fibers*, 1987 Ultrasonic Symposium, pp. 443-453.

C. K. Jen, *Similarities and Differences Between Fiber Acoustics and Fiber Optics*, 1985 Ultrasonics Symposium, pp. 1128-1133.

A. Safaai-Jazi, et al, *Analysis of Liquid-Core Cylindrical Waveguides*, Journal of Acoustical Society of America, V. 81, No. 5, May, 1987, pp. 1273-1278.

C. K. Jen, et al, *Longitudinal Modes in Weakly Guiding Fiber Acoustic Waveguides*, 1985 Ultrasonics Symposium, pp. 1134-1138.

John E. May, *Wire Type Dispersive Ultrasonic Delay Lines*, IRE Transactions on Ultrasonics Engineering, Jun., 1960, pp. 44-53.

*Primary Examiner*—William E. Kamm
*Assistant Examiner*—George Manuel

[57] ABSTRACT

An intracavity ultrasound diagnostic probe has a fiber acoustic waveguide that guides acoustic signals generated by a piezoelectric transducer located outside the body, through a body cavity and to an imaging site within the body where they reflect back into the ultrasound diagnostic probe that guides them back to the piezoelectric transducer located at the proximal end of the waveguide. The intracavity ultrasound diagnostic probe has one or more acoustic waveguides that could be optical fibers. The numerous advantages of placing the piezoelectric transducer outside the body include: electric power does not enter the body; a reusable piezoelectric transducer; the ability to use several acoustic signals at once including a mixture of doppler and imaging acoustic signals; the ability to adjust the frequency of each acoustic signal independently of the other acoustic signals to obtain the most desirable focus and resolution for a particular imaging site; and lower cost of complying with sterility regulations since they require discarding only the inexpensive fiber acoustic waveguide and the inexpensive catheter-radome.

40 Claims, 8 Drawing Sheets

INTRACAVITY ULTRASOUND DIAGNOSTIC PROBE USING FIBER ACOUSTIC WAVEGUIDES

This is a continuation-in-part application of a copending application Ser. No. 579,428 filed on Sep. 7, 1990, issued on Oct. 6, 1992 into U.S. Pat. No. 5,152,291, entitled ACOUSTIC FIBER MEASUREMENT OF INTRAVASCULAR BLOOD, filed in the name of J. Fleming Dias, and owned by the assignee of this application. Also this application is a continuation-in-part of another copending application Ser. No. 332,517, filed on May 16, 1989, issued Jun. 8, 1993 into U.S. Pat. No. 5,217,018, entitled ACOUSTIC TRANSMISSION THROUGH CLADDED CORE WAVEGUIDE (previously entitled An Ultrasonic Catheter Guidance System), filed in the name of J. Fleming Dias, and owned by the assignee of this application.

FIELD OF THE INVENTION

The invention relates generally to the field of ultrasound diagnostic probes and more specifically to the field of invasive ultrasound diagnostic probes.

BACKGROUND OF THE INVENTION

Figure 14:
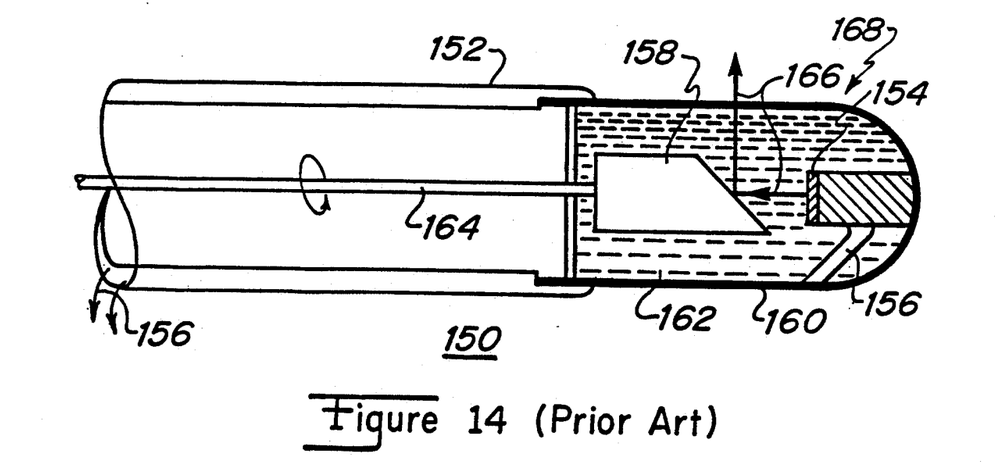
FIG. 14 shows a previously existing imaging catheter with a piezoelectric transducer at the distal end.

FIG. 14 shows the basic construction of a previously known imaging probe. The imaging probe 150 consists of a catheter 152, a piezoelectric transducer 154 (i.e., a transducer having a material that electrically polarizes when mechanically strained and that mechanically strains when electrically polarized) at the distal end 168 of catheter 152 (i.e., the end of the catheter that goes into the body), electric wires 156 that connect piezoelectric transducer 154 to external circuitry at the proximal end (i.e., the end that stays outside the body), an acoustic reflector 158 (i.e., a mirror), a rotating drive shaft 164 coupled to a small motor/shaft encoder at the proximal end, an acoustic reflector 158 at the distal end, and a plastic radome 160 (i.e., an acoustic window that has the same acoustic impedance as a fluid) filled with a liquid 162 that fits over piezoelectric transducer 154 and acoustic reflector 158.

Piezoelectric transducer 154 is stationary and when excited by an external source, it produces an acoustic signal 166 that travels through the liquid in radome 160 and strikes acoustic reflector 158. The surface of acoustic reflector 158 resides at an angle of 45° from acoustic signal 166 and it reflects acoustic signal 166 at an angle of 90° from its original path. The reflected acoustic signal 166 travels through liquid 162 in radome 160 and propagates through the blood until it encounters the artery wall.

Depending on the penetration, several echoes return to piezoelectric transducer 154 by retracing essentially the same path. Piezoelectric transducer 154 converts these echoes into corresponding electrical pulses. And wires 156 carry these electrical pulses to electrical circuitry located at the proximal end. Since acoustic reflector 158 continuously rotates, acoustic signal 166 continuously rotates. Echoes from each angular position are collected, processed and displayed on a CRT screen.

Previously known imaging probes have variations of the configuration shown by FIG. 14. In an alternate configuration, the acoustic reflector 158 and piezoelectric transducer 154 exchange places. These and other configurations have the following in common: all use a piezoelectric transducer at the distal end of the catheter, which goes inside the body.

Placing the piezoelectric transducer at the distal end of the catheter that goes inside the body has numerous disadvantages. The piezoelectric transducer may emit leakage currents inside the body that can induce fibrillation when the probe images a coronary artery. Wires 156 that connect the piezoelectric transducer to external circuitry inherently act as antennas and they receive radio frequency (RF) interference present in a catheterization laboratory. This RF interference appears as noise in the electrical signals that travel to and from the piezoelectric transducer and increases the risk that these electrical signals may cause fibrillation.

Another disadvantage of placing the piezoelectric transducer at the distal end of the catheter that goes inside the body is that the piezoelectric transducer has a frequency of operation determined by its thickness. The user cannot adjust the piezoelectric transducer frequency to obtain a more desirable resolution or to illuminate a particular region of interest.

Another disadvantage of placing the piezoelectric transducer at the distal end of the catheter is that after one use the piezoelectric transducer must be discarded along with the catheter to prevent the transmission of disease. This is burdensome because the piezoelectric transducers are difficult and expensive to make. It also discourages use of the most desirable transducers because they usually are more expensive. Generally, increasing the frequency of the acoustic waves improves the resolution capability of the transducer, but it also increases the expense because the output frequency of piezoelectric transducers depends upon their thickness (i.e., a 40 MHz piezoelectric transducer would have a thickness of approximately 2 mils) and the thinner the transducer, the more expensive the transducer.

SUMMARY OF THE INVENTION

For the reasons previously discussed, it would be advantageous to have an intracavity ultrasound diagnostic probe that uses a piezoelectric transducer located outside the body.

The present invention is an intracavity ultrasound diagnostic probe that has one or more acoustic waveguides, each having a proximal end acoustically coupled to an acoustic signal generator (i.e., piezoelectric transducer) located outside the body and that generates one or more emitted acoustic signals (i.e., any acoustic signal, Doppler, imaging, etc.). The waveguides have a wide bandwidth and can simultaneously propagate several acoustic signals that have distinct frequency bands. The intracavity ultrasound diagnostic probe guides one or more emitted acoustic signals through a body cavity (i.e., a naturally occurring cavity such as a blood vessel or the esophagus or a surgical bore) to the distal end of the intracavity ultrasound probe inside the body where it has a distal end port through which the emitted acoustic signals leave the ultrasound diagnostic probe. The emitted acoustic signals echo off the body (e.g., wall of a coronary artery) and become reflected acoustic signals. The reflected acoustic signals reenter the intracavity ultrasound diagnostic probe through the distal end port and the probe guides these signals back through the body cavity to the proximal end and to an acoustic detector (i.e., piezoelectric transducer) located outside the body.

The entire intracavity ultrasound probe can rotate or not rotate. The rotation can be continuous when forming images of a cross section of the body cavity, can be stepped (i.e., probe rotates to a certain position, stays there while measurements are made, then rotates again) when measuring the cross-sectional area of a blood vessel, or can be irregular when needed, such as, aiming an acoustic signal down a particular branch blood vessel.

By placing the piezoelectric transducer outside the body, this invention has the advantage of eliminating electric wires and electric power from inside the body and eliminating the risk of potentially dangerous leakage currents. This advantage is particularly noteworthy for ultrasound probes that use several acoustic signals. By eliminating electric power from inside the body, the present invention opens up the possibility of making ultrasonic images from inside the brain without the aforementioned risk.

A further advantage of using acoustic fibers to guide acoustic signals generated outside the body is the lower cost of these ultrasound diagnostic probes especially those that emit and detect several acoustic signals. Instead of disposing of a piezoelectric transducer and two connecting wires for each acoustic signal, the present invention requires the disposal of approximately two meters of acoustic fiber.

Another advantage of placing the piezoelectric transducer outside the body is that a user can choose a transducer for its ability to produce a desired acoustic signal or a range of desired acoustic signals. Alternatively, the user can replace a transducer with another transducer. Thus, a user can choose high performance transducers not previously available for intracavity ultrasound probes, such as, variable frequency piezoelectric transducers that allow the user to vary the frequency of the acoustic signal.

The user may want to vary the frequency of the emitted acoustic signal for many reasons. The user may want to characterize tissue (i.e., decide what type of tissue is there), examine the interior of a lesion, or measure the bore of a blood vessel. Generally, higher frequency acoustic signals produce higher resolution images. However, a higher frequency acoustic signal may experience significant energy loss as it travels through the tissue. Some, high frequency acoustic signals may provide a high resolution picture of the surface of the lesion, but it cannot penetrate the lesion at all.

With the present invention, the user can vary the frequency of the acoustic signal to examine the interior layers of the lesion. Alternatively, if the user is measuring the width of the blood vessel, a high frequency acoustic signal that cannot penetrate the blood vessel wall may be desired. Thus, an advantage of the present invention is that the user can vary the frequency until the acoustic signal produces an optimum picture at a given location and a given depth.

An ultrasound probe that emits and detects several acoustic signals can use multiple acoustic frequencies to create multiple cross sections of the body tissue (e.g., the walls of blood vessel) at one location but at different depths. This is feature is particularly valuable when investigating lesions inside blood vessels because they can change abruptly.

Alternatively, the acoustic signals can be aimed in different directions such as ahead of the distal end of the ultrasound diagnostic probe, next to the distal end of the ultrasound diagnostic probe, and behind the distal end of the ultrasound diagnostic probe. This is valuable for probes that cut or compress plaque inside arteries or perform other operations inside the body because it allows the user to look at lesions ahead of the probe, inspect the performance of operations beside the probe, and look behind the probe to check the removal of the lesion.

DETAILED DESCRIPTION OF THE INVENTION

Figure 1:
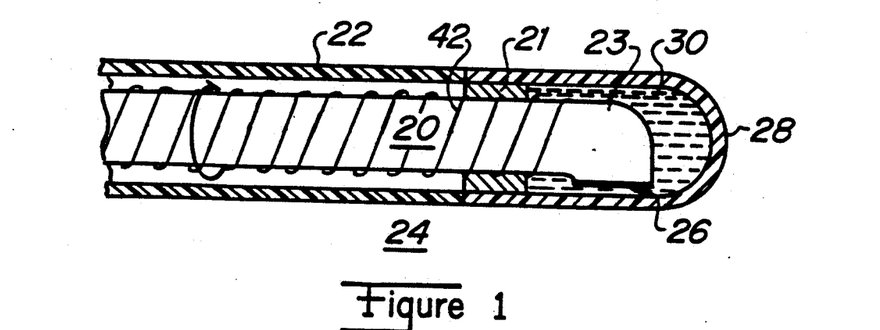
FIG. 1 shows the distal end of an intracavity ultrasound diagnostic probe using one acoustic waveguide.

FIG. 1 shows the distal end 24 of a catheter containing an intracavity ultrasound diagnostic probe 20 that enters the body through a naturally occurring body cavity such as a blood vessel or a man-made bore hole in the skull. In FIG. 1, one-half of a catheter 22, a support 21, and a fluid supply 30 have been cut away to show ultrasound diagnostic probe 20. Intracavity ultrasound diagnostic probe 20 in FIG. 1 is a rotating acoustic waveguide with a distal end port 26 inside a fluid filled radome 28. A wire 42 reinforces ultrasound diagnostic probe 20 and a support 21 lifts ultrasound diagnostic probe 20 off the wall of catheter 22 to facilitate its rotation. A radome 28 and catheter 22 covers and protects ultrasound diagnostic probe 20. Radome 28 is an acoustic window that has an acoustically opaque line. When an acoustic fiber rotates past the acoustically opaque line, the acoustically opaque line encodes its position.

Near distal end port 26, ultrasound diagnostic probe 20 has a bend 23 that rotates about the longitudinal axis of the ultrasound diagnostic probe and causes the main acoustic beam to rotate in a circular trajectory. Bend 23 has an angle that can be either greater, smaller, or equal to 90°. An impedance matching layer coats distal end port 26 and causes the output acoustic impedance of ultrasound diagnostic probe 20 to match the acoustic impedance of fluid 30 inside radome 28 so the acoustic energy loss is minimized and the amount of energy transferred to the body is maximized. The impedance matching layer is any material, such as an epoxy, whose acoustic impedance, $Z_{ML}$, is approximately equal to $(Z_O * Z_L)^{\frac{1}{2}}$ where $Z_O$ is the acoustic impedance of the acoustic fiber and $Z_L$ is the acoustic impedance of fluid 30 inside radome 28. In the preferred embodiment of the invention radome 28 and fluid 30 are identical with those found in previously known imaging probe catheters such as that shown in FIG. 14. Fluid 30 is a sterile saline solution.

Figure 2:
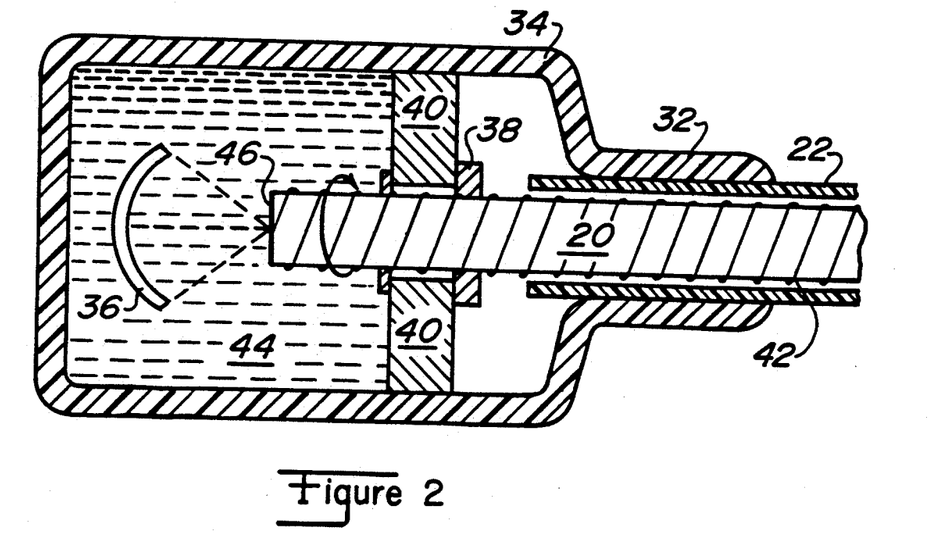
FIG. 2 shows the proximal end of the intracavity ultrasound diagnostic probe shown in FIG. 1.

FIG. 2 has removed a portion of housing 34 and shows proximal end 46 of intracavity ultrasound diagnostic probe 20 and the hardware that drives it. Also, FIG. 2 has removed a portion of catheter 22 and shows ultrasound diagnostic probe 20. Proximal end 46 and the hardware inside housing 34 always remain outside the body. Housing 34 is an extruded plastic part. Catheter 22 and intracavity ultrasound diagnostic probe 20 fit through a neck 32 of housing 34 that encloses a piezoelectric transducer 36 and a motor 40. Intracavity ultrasound diagnostic probe 20 extends beyond catheter 22 and through a hole cut in the center of a shaft 38 of motor 40. Since motor 40 does not enter the body, it could be any of a variety of readily available motors.

Ultrasound diagnostic probe 20 bonds to shaft 38 and its entire length rotates when shaft 38 rotates so that distal end port 26 shown in FIG. 1 makes a circular sweep over the circumference of the body cavity. Motor 40 can rotate ultrasound diagnostic probe 20 continuously, or in a reciprocating circular motion to generate a sector scan, or in step-wise circular motion, or at the will of the user without departing from the scope of the invention. When imaging the interior of a body cavity the probe rotates continuously.

Ultrasound diagnostic probe 20 extends beyond motor 40 into a saline solution that fills chamber 44 that also has a spherically-shaped piezoelectric transducer 36 attached to housing 34. A spherically-shaped piezoelectric transducer is a shell of piezoelectric crystal material that is machined to the desired thickness and radius of curvature. The thickness of the transducer shell governs the frequency of the output acoustic signal and radius of curvature the transducer shell governs the focal point. Both the convex and the concave surfaces are metallized with chromium and gold films. Then, the transducer shell is poled by applying a voltage of 3,200 volts per mm of shell thickness. U.S. patent application Ser. No. 07/352,517, filed May 16, 1989, on an invention of J. Fleming Dias entitled "Ultrasonic Catheter Guidance System" discusses other means of focusing ultrasonic energy into the acoustic waveguide.

The proximal end 46 of ultrasound diagnostic probe 20 is located at the focal point of spherically-shaped transducer 36. The fluid inside chamber 44 couples acoustic signals to ultrasound diagnostic probe 20. If the acoustic impedance of ultrasound diagnostic probe 20 differs from the acoustic impedance of the fluid, an impedance matching layer coats proximal end 46 and matches the output acoustic impedance of ultrasound diagnostic probe 20 with the acoustic impedance of the fluid. This impedance matching layer is similar to the previously discussed impedance matching layer.

To form ultrasonic images of the interior of a coronary artery or other cavity in the body, distal end 24 of the ultrasound diagnostic probe travels through a body cavity until it reaches an imaging site. Shaft 38 of motor 40 rotates the entire ultrasound diagnostic probe 20 so that distal end port 26 has a circular trajectory around the center of the coronary artery or other cavity. Meanwhile, electrical signals drive spherical piezoelectric transducer 36 so that it generates emitted acoustic signals that have a frequency preferably between 10 MHz and 50 MHz and that are focussed at the proximal end 46 of ultrasound diagnostic probe 20.

The emitted acoustic signals enter ultrasound diagnostic probe 20 and travel its length to distal end port 26 where it leaves ultrasound diagnostic probe 20 and travels through body fluids until it encounters a change in the acoustic impedance. This occurs when the emitted acoustic signal strikes body tissue. The reflected acoustic signal travels back to distal end port 26 and enters image probe 20. The reflected acoustic signal propagates the length of ultrasound diagnostic probe 20 and strikes piezoelectric transducer 36 that converts the reflected acoustic signal into an electric signal that contains information on the contours of the inside surface of the body cavity. The echoes from each angular position are collected, processed and displayed on a CRT screen as a 2-D cross-sectional image.

Figure 3:
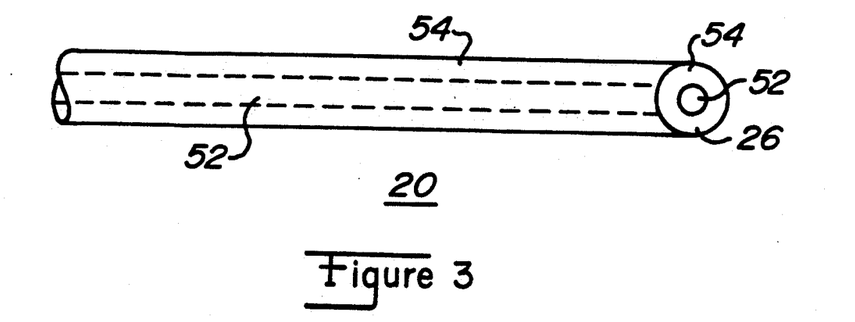
FIG. 3 shows the front elevation looking into the distal end port at the distal end of the ultrasound diagnostic probe shown in FIG. 1.

FIG. 3 shows the front elevation of the distal end of ultrasound diagnostic probe 20 looking into its distal end port 26. Ultrasound diagnostic probe 20 is an acoustic waveguide. In general, an acoustic waveguide is similar to an optical waveguide, i.e., optical fiber. Both acoustic fibers and optical fibers typically have a central core 52 and an outer cladding 54 that surrounds core 52 and is in intimate acoustic contact with it. The purpose of the cladding is to keep the acoustic signals within the acoustic fiber core. When the materials for the cladding and the core meet the specifications described below, the fiber guides the acoustic signals because they bounce off the cladding and stay inside the core. C. K. Jen has described the acoustical transmission line in a paper entitled "Similarities and Differences Between Fiber Acoustics and Fiber Optics" in *IEEE Ultrasonics Symposium*, Oct. 15-16, 1985.

The diameter of a "single mode acoustic fiber" equals the diameter of a multimode "optical fiber" because acoustical wavelengths, $\lambda_a$, at operating frequencies between 10 and 100 MHz are much larger than the optical wavelengths, $\lambda_o$. For this reason and the availability of optical fibers, experiments in fiber acoustics utilize glass optical fibers and the preferred embodiment of the invention uses optical fibers for ultrasound diagnostic probes 20. But any number of materials could form core 52 and outer cladding 54. For example, ultrasound diagnostic probe 20 could be a stainless steel core with a suitable metal cladding electroplated or sputtered around the core, or the ultrasound probe could have a liquid core and a solid capillary tube acting as the cladding.

The cladded-core acoustic fiber of ultrasound diagnostic probe 20 supports several modes, but the mode of interest to the present invention is the predominantly longitudinal mode. It is not strictly of a guided nature and therefore somewhat lossy. The preferred embodiment of ultrasound diagnostic probe 20 has a length around two meters and the loss sustained over two meters is tolerable. These longitudinal modes can be ideally guided by core and cladding materials that have equal shear wave velocities, i.e., $V_{SCO} = V_{SCL}$ and $\rho_{CO} = \rho_{CL}$, where $V_S$ is the shear velocity, $\rho$ is the density, CO refers to the core, and CL refers to the cladding.

To obtain an acoustic fiber for the ultrasound diagnostic probe 20 with minimum attenuation for longitudinal modes, the following must be minimized:

1. The shear wave velocity difference $\epsilon_g$, between core and cladding must be much less than unity:

$$\epsilon_g = \frac{V_{SCL} - V_{SCO}}{V_{SCO}} << 1.$$

2. The density difference between the core and cladding must also be much less than unity:

$$\epsilon_\rho = \frac{\rho_{CL} - \rho_{CO}}{\rho_{CO}} << 1$$

and when $\epsilon_g = \epsilon_\rho = 0$, the modes are tightly bound to the core and the transmission loss is minimum.

For the existence of the longitudinal modes, the following condition must also be satisfied.

$$\epsilon_L = \frac{V_{LCL} - V_{LCO}}{V_{LCO}} << 1$$

but $\neq 0$ where $V_L$ is the longitudinal velocity.

Since most multimode glass optical fibers satisfy the above conditions, the preferred embodiment of the present invention uses them as acoustic waveguides for ultrasound pulses. This disclosure uses glass optical fibers to illustrate the operation of several embodiments of an ultrasound diagnostic probe.

Wire 42, of FIG. 1, increases the torsional strength of ultrasound diagnostic probe 20 so that it can rotate as a drive shaft. Wire 42 is stainless steel wire having a diameter between 150 μm and 250 μm. It is helically wrapped around a mandrel that has nearly the same diameter as the acoustic waveguide. If the ultrasound probe has one acoustic fiber, then the diameter of the mandrel should be equal to the diameter of the acoustic fiber. The helically-wrapped wire 42 is slid off the mandrel and onto ultrasound diagnostic probe 20. A mandrel with a triangular section can be used when probe 20 consists of one fiber in the center and three other fibers arranged around it and angularly spaced by 120°. Other means for reinforcing ultrasound diagnostic probe 20 or any other probe or variation of any probe described herein are within the scope of the present invention.

Figure 4:
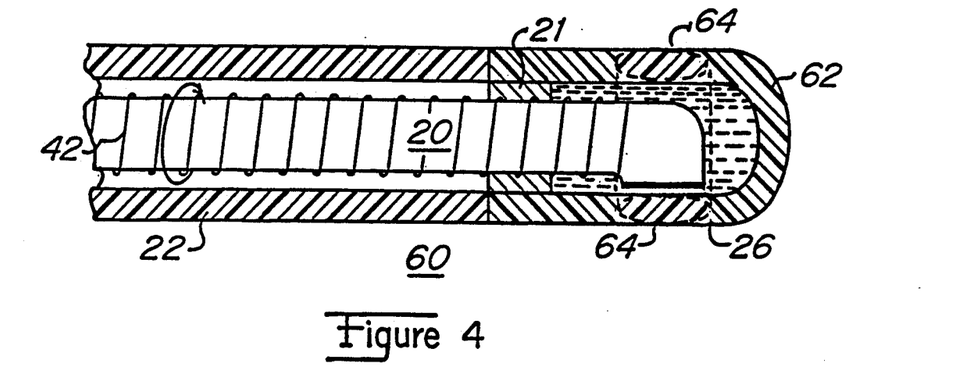
FIG. 4 shows the distal end of a catheter having a radome with an integral lens. The radome is filled with sterile saline solution.

FIG. 4 shows an alternate embodiment of the invention that has a cylindrical fixed focus lens 64 around the entire periphery of radome 62. When the acoustic signal leaves fiber 20 it spreads out in a conical fashion. This reduces the amount of acoustic energy at the imaging site. Lens 64 focuses part of the acoustic signal after it leaves fiber 20 to prevent this loss of acoustic energy. Lens 64 is formed during the extrusion process that forms radome 62. The curvature of the lens depends on the acoustic velocity of the material that forms lens 64 and the acoustic velocity of blood surrounding the lens.

A lens could be attached to distal end port 26 of ultrasound probe 20 in FIG. 1. An impedance matching layer located between the fiber and the lens would match the acoustic impedance of the lens to the acoustic impedance of fluid 30.

The lens would have a roughly circular cross section and a roughly spherical shape and would be capable of focusing the entire acoustic signal.

In FIG. 1, ultrasound diagnostic probe 20 has a bend 23 that directs the acoustic beam at an angle to the axis of rotation. Bend 23 increases the maximum diameter of ultrasound diagnostic probe 20. This increase may be large enough to prevent ultrasound probe 20 from entering some coronary arteries.

Figure 5A:
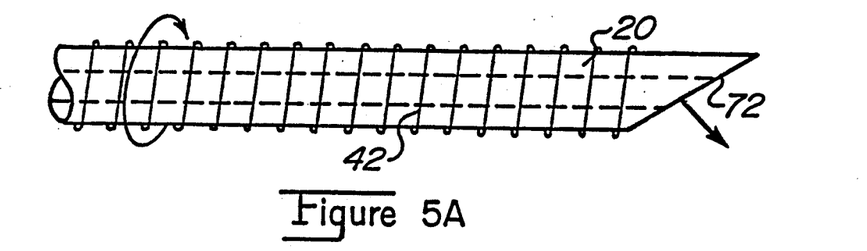
FIGS. 5A and 5B show embodiments of the ultrasound diagnostic probe that aim the acoustic beam without bending the fiber.
Figure 5B:
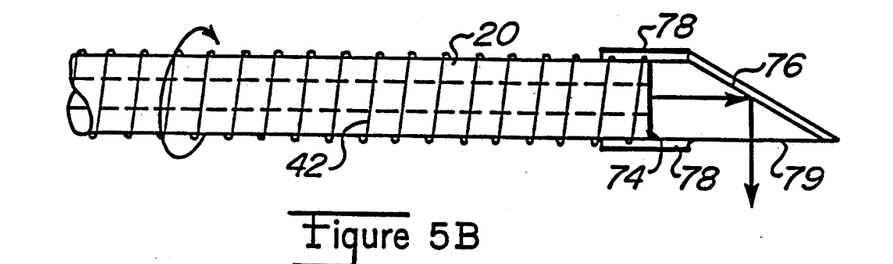
Figure 13A:
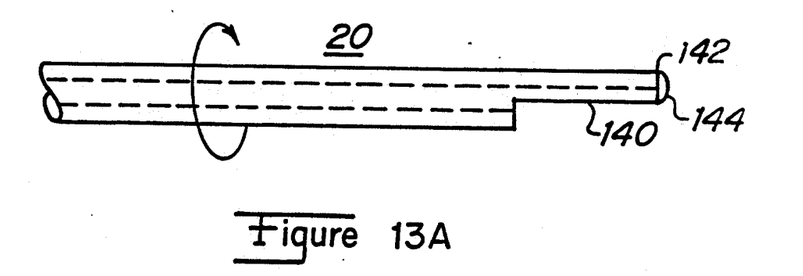
FIGS. 13A and 13B show an alternate embodiment of the acoustic waveguide with a portion of the core removed so the acoustic signal exits from the side of the waveguide.
Figure 13B:
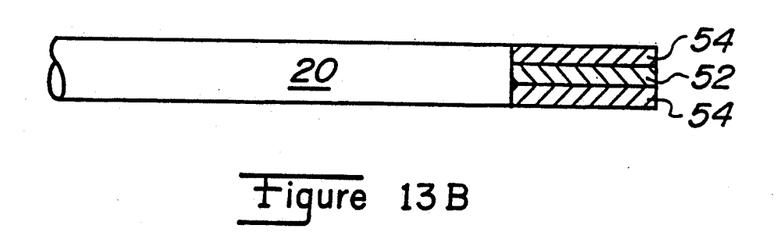

FIG. 5A and 5B show two ways to direct the acoustic beam without increasing the diameter of ultrasound diagnostic probe 20 so that catheter 22 may enter blood vessels having a diameter slightly larger than that of ultrasound diagnostic probe 20. FIG. 13A and 13B show another way to direct the acoustic signal without increasing the diameter of ultrasound probe 20.

FIG. 5A shows ultrasound diagnostic probe 20 with a bevelled distal end port 72. FIG. 5B shows ultrasound diagnostic probe 20 having a distal end port 74 with a surface perpendicular to the axis of ultrasound diagnostic probe and an acoustic reflector 76 that directs the acoustic beam at an angle to the axis of rotation. A housing 78 attaches acoustic reflector 76 to ultrasound diagnostic probe 20 so that it rotates with the ultrasound diagnostic probe. Housing 78 has an acoustic window for the acoustic beams.

In FIGS. 13A and 13B a distal end port 140 is parallel to the longitudinal axis of the fiber. It is formed by exposing a large area of core 52 by cutting away all of cladding 54 from a portion of fiber 20 and part of core 52. An impedance matching layer discussed earlier coats distal end port 140. An acoustic absorber 144 may be applied to end face 142 to prevent undesired reflections. The acoustic absorber 144 is a mixture of epoxy glue mixed with very fine teflon powder. Removal of the cladding destroys the guided nature of the longitudinal mode of fiber 20 near distal end port 140 so that acoustic pulses can exit the fiber through distal end port 140. This version of the distal end port can be utilized in all the embodiments disclosed in this application.

Figure 6:
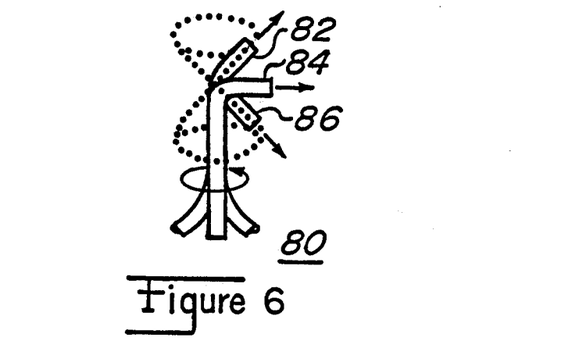
FIG. 6 is a side view of another embodiment of a vascular ultrasound diagnostic probe with three cladded-core acoustic waveguides.

Ultrasound diagnostic probe 20 can have multiple fibers as shown in FIGS. 6-12. FIG. 6 shows an ultrasound diagnostic probe 80 useful for imaging the artery along non-parallel planes. Ultrasound diagnostic probe 80 has three acoustic fibers 82, 84, 86 bent to direct their respective acoustic beams in three different directions. Look-to-the-side acoustic fiber 84 provides a cross sectional image at approximately 90° to the longitudinal axis of the artery. Look-ahead acoustic fiber 82 rotates along a conical surface in front of the catheter and images what is in front of the catheter. Look-behind acoustic fiber 86 rotates along a conical surface behind the other fibers and possibly a plaque compression tool or a plaque removal tool. Look-behind acoustic fiber 86 shows what has been done. FIG. 6 shows acoustic fibers 82 and 86 spaced 90° apart but they could be spaced differently without departing from the scope of the invention. These embodiments would be useful with catheters used in balloon angioplasty and in atherectomy devices such as the Rotablator described in *Design News* of Sep. 23, 1991. Forward-looking acoustic fiber 82 shows what will be cut or compressed, acoustic fiber 84 shows what is being cut or compressed, and backward-looking acoustic fiber 86 shows what has been cut.

Figure 7A:
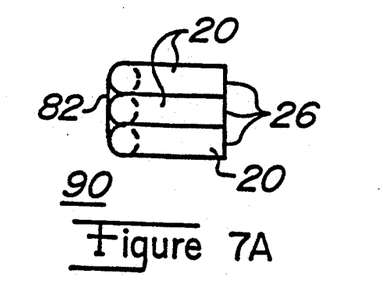
FIG. 7A is a top view and FIG. 7B is a side view of an intravascular ultrasound diagnostic probe with three cladded-core acoustic waveguides with distal ends in different horizontal planes but aimed in the same radial direction.
Figure 7B:
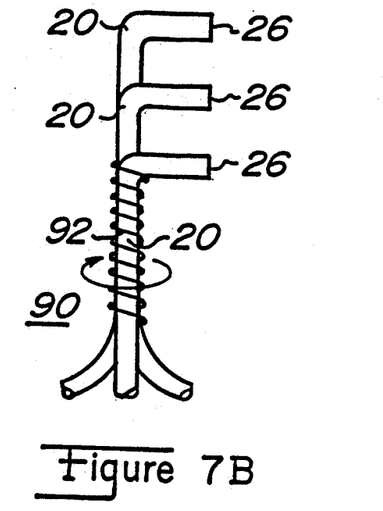

FIG. 7A shows the top view and FIG. 7B shows the side view of an ultrasound diagnostic probe 90 that takes three cross sections at once and gives a composite view of the blood vessel. Lesions can change dramatically and taking three cross sections at once helps to illuminate these differences. If the catheter moves a precise amount between cross sections, then the cross sections can be correlated and a computer could form a three dimensional image of the blood vessel. A reinforcement wire 92 wrapped around ultrasound diagnostic probe 90 gives it adequate reinforcement so it can rotate as a drive shaft. Reinforcement wire 92 is made in the same manner that reinforcement wire 42 is made. Other embodiments of this ultrasound diagnostic probe have two, four, five, etc. acoustic fibers without departing from the scope of the invention.

Figure 8A:
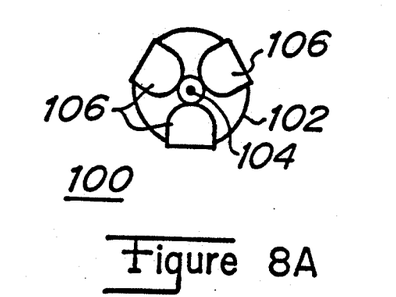
FIG. 8A is a top view and FIG. 8B is a side view of the distal end of an intravascular ultrasound diagnostic probe that has three cladded-core acoustic waveguides with distal ends in the same horizontal plane but spaced angularly and another cladded-core acoustic waveguide in the center.
Figure 8B:
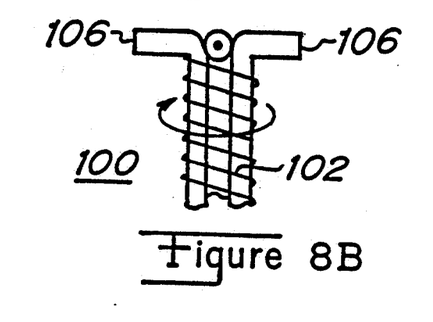

FIG. 8A shows a top view and FIG. 8B shows a side view of another embodiment of the invention. Ultrasound diagnostic probe 100 has three acoustic fibers 106 that aim acoustic signal in the same radial plane (i.e., plane located perpendicular to the longitudinal axis of the ultrasound probe) but approximately 120° apart. Reinforcement wire 102 is similar to reinforcement wire 42 shown in FIG. 1 except that its cross section that equals the cross section of ultrasound diagnostic probe 100. The acoustic signals can have the same frequency and image the entire body cavity cross section with 120° rotation of the probe. The acoustic signals can have different frequencies and each acoustic signal would image different depths of the same cross section. The ultrasound probe could have any number of acoustic fibers that aim their acoustic signal in any direction without departing from the scope of the invention. Also, ultrasound probe 100 could have a center acoustic fiber 104 for making doppler measurements.

Figure 9:
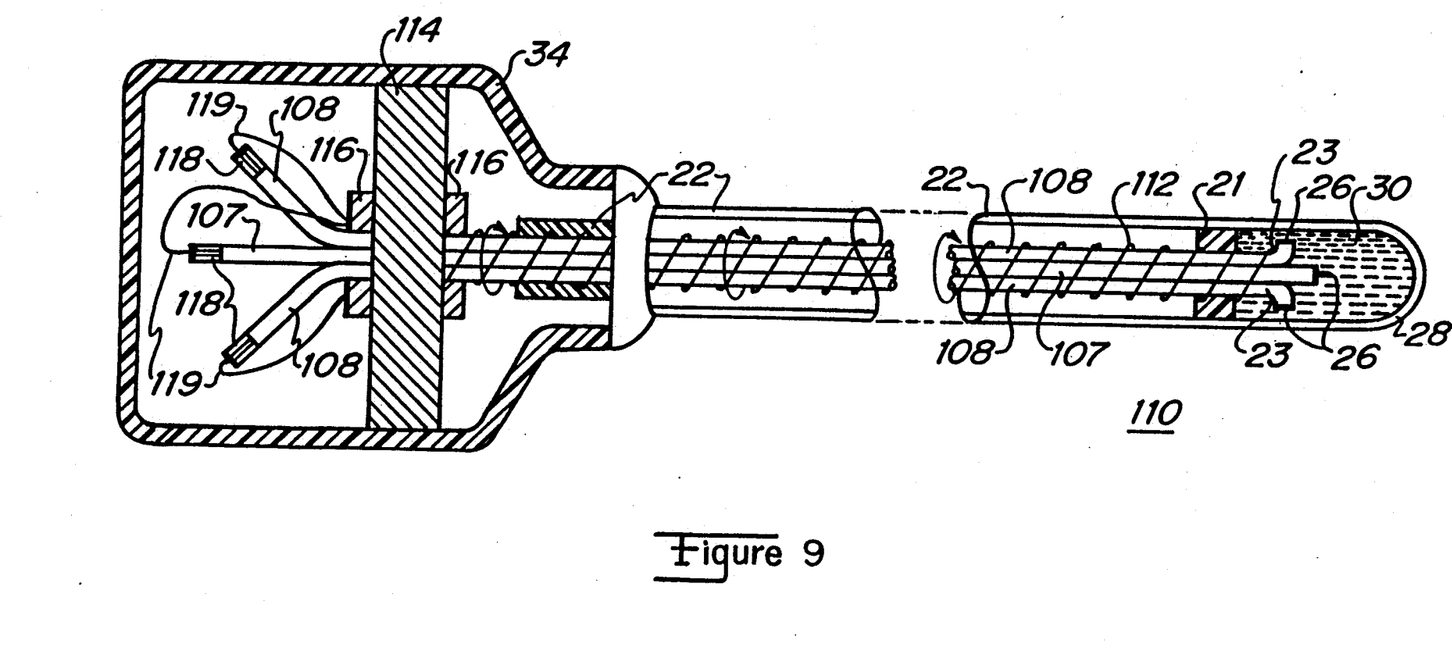
FIG. 9 shows the distal and the proximal end of the preferred embodiment of the ultrasound diagnostic probe inside its housing.
Figure 10:
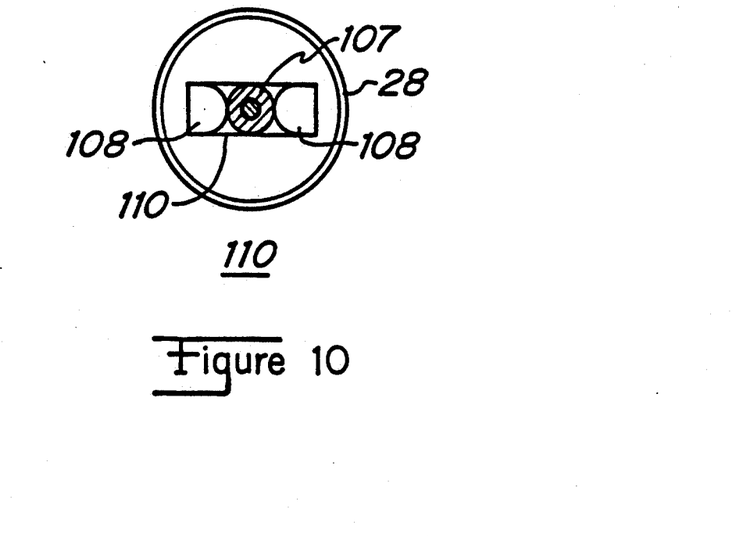
FIG. 10 shows the top view of the distal end of the preferred embodiment intracavity ultrasound diagnostic probe shown in FIG. 9.

FIGS. 9 and 10 show a combination probe 110 that is the preferred embodiment of the invention. FIG. 10 shows a top view of combination probe 110 shown in FIG. 9. Combination probe 110 is a combination doppler and imaging probe. It has a center acoustic fiber 107 that has the same structure and properties as previously described acoustic fibers except that it aims the acoustic beam straight ahead. Center acoustic fiber 107 guides emitted acoustic signals from a piezoelectric transducer 118 located outside the body, through blood vessels to a distal end port 26 and straight into the blood vessel.

These emitted acoustic signals reflect off the red blood cells to form reflected acoustic signals that have a shifted frequency. The reflected acoustic signals re-enter center acoustic fiber 107 through distal end port 26 that guides them back through the blood vessels to piezoelectric transducer 118. A computer processes these signals to determine the net frequency shift and the velocity of the blood.

The following equation gives the net frequency shift:

$$f_D = 2f_T \frac{V\cos\theta}{C};$$

where $f_D$ = doppler shift in frequency of the reflected acoustic signal;
$f_T$ = frequency of the emitted acoustic signal;
$C$ = velocity of sound in blood (1560 m/s)
$\theta$ = angle of the emitted acoustic signal and the velocity vector of the blood; and
V velocity of blood flow.

In the case of intravascular doppler measurements, the catheter is almost collinear with the blood flow and therefore $\theta$ is approximately 0, and thus, $$f_D \approx \frac{2f_T V}{C}.$$

Ultrasound diagnostic probe 110 has two modes of operation for measuring the velocity of blood flow: a continuous wave mode and a pulsed wave mode.

Figure 15:
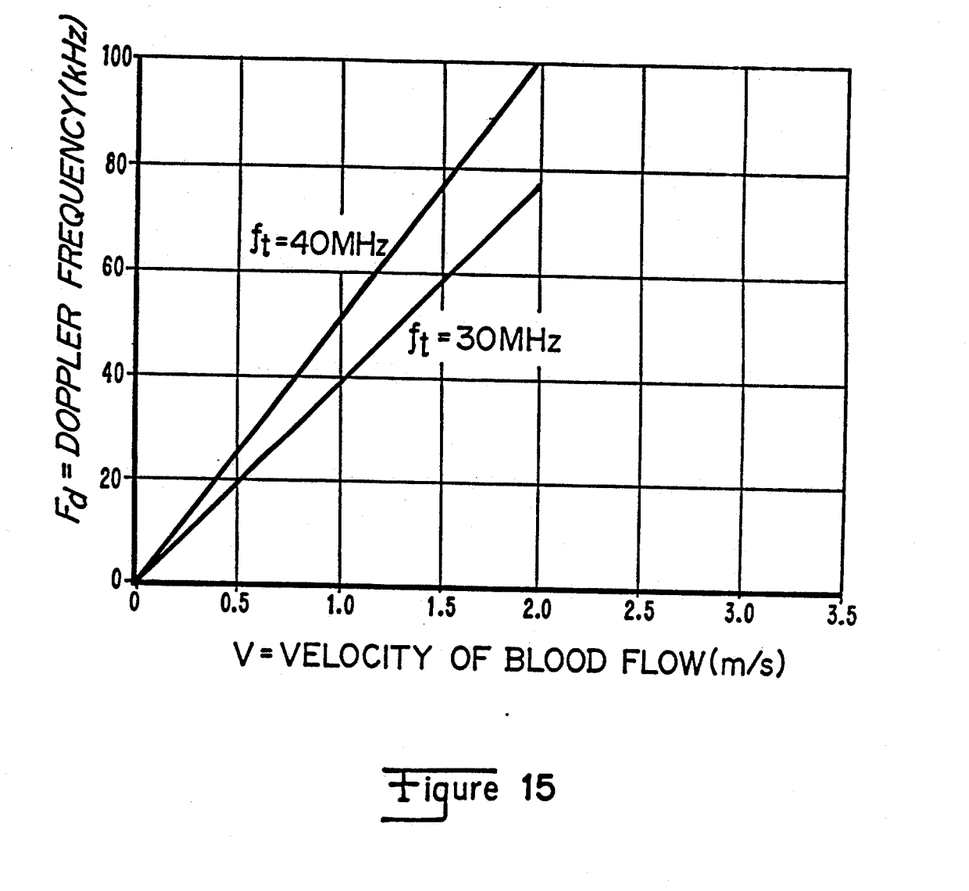
FIG. 15 is a graph depicting the relationship between doppler frequency and blood flow velocity for two alternative frequencies.

Continuous wave mode obtains an estimate of blood velocity. In this mode, the reflected acoustic signals come from the full extent of the emitted acoustic signal and therefore, while no range resolution is possible, there is no limit on the maximum velocity that can be measured. FIG. 15 depicts a graph showing velocity of blood flow versus doppler shift frequency corresponding to excitation acoustic signals having a frequency, $f_T$ equal to 30 MHz and 40 MHz respectively.

An advantage of the ultrasound diagnostic probe is the wide bandwidth of the acoustic fibers that permit the use of very high frequency emitted acoustic signals for both doppler and imaging application. Because of the ability to use much higher frequency emitted acoustic signals, it is possible to measure very low blood flow velocities. For example, as shown in FIG. 15, using a 40 MHz emitted acoustic signal, blood flow velocity of approximately 0.25 m/s results in a 16 kHz Doppler shifted reflected acoustic signal.

Copending U.S. patent application Ser. No. 07/579,428, filed Sep. 7, 1990, on an invention of J. Fleming Dias entitled "Acoustic Fiber Measurement of Intravascular Blood" and assigned to the Hewlett-Packard Company describes the use of acoustic fibers to measure the velocity of blood.

Figure 11:
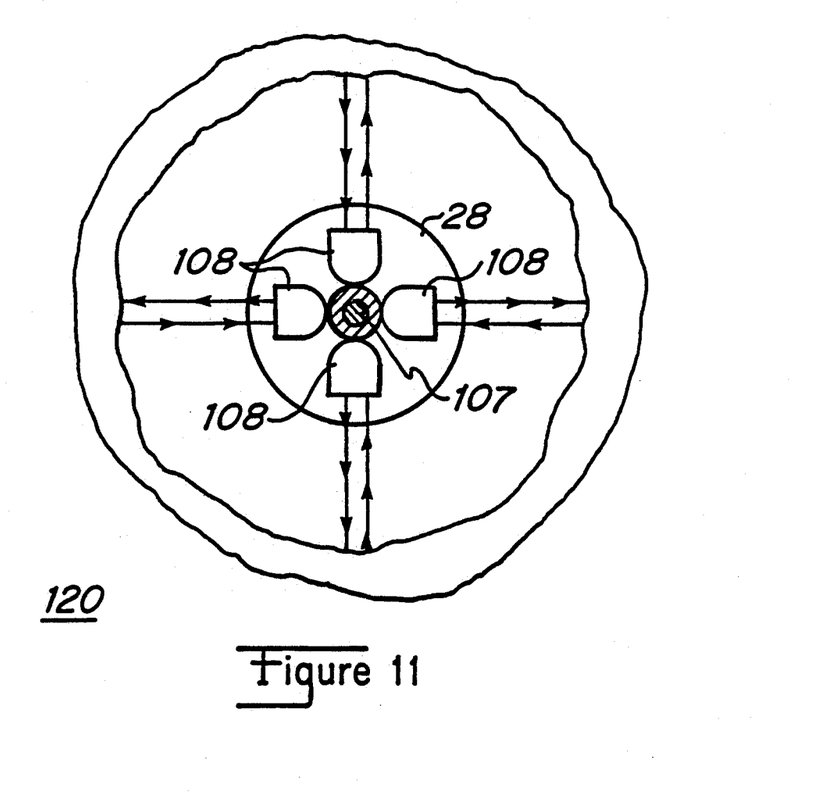
FIG. 11 shows the top view of an alternate embodiment of the invention that has four imaging acoustic fibers and one Doppler acoustic fiber at the center.
Figure 12A:
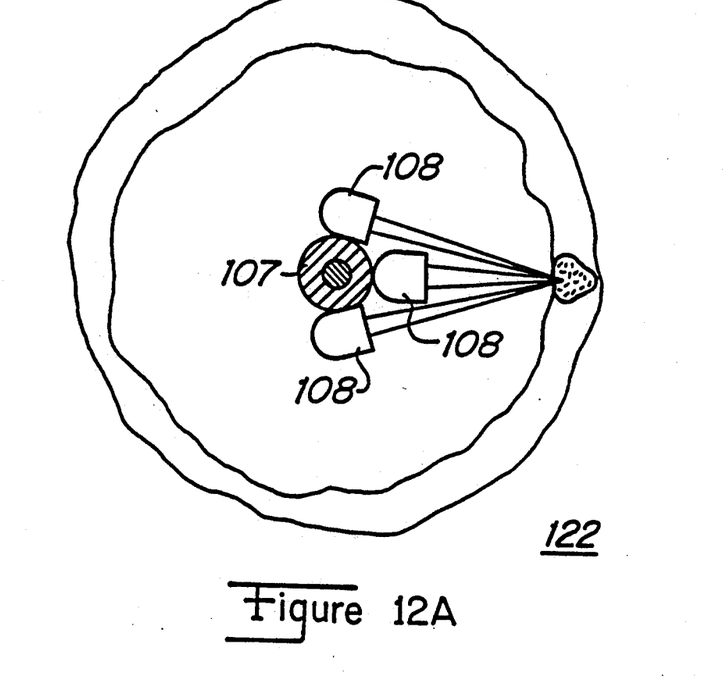
FIG. 12A shows the top view of an alternate embodiment of the invention that has three acoustic waveguides that emit acoustic signals that insonify the same spot.
Figure 12B:
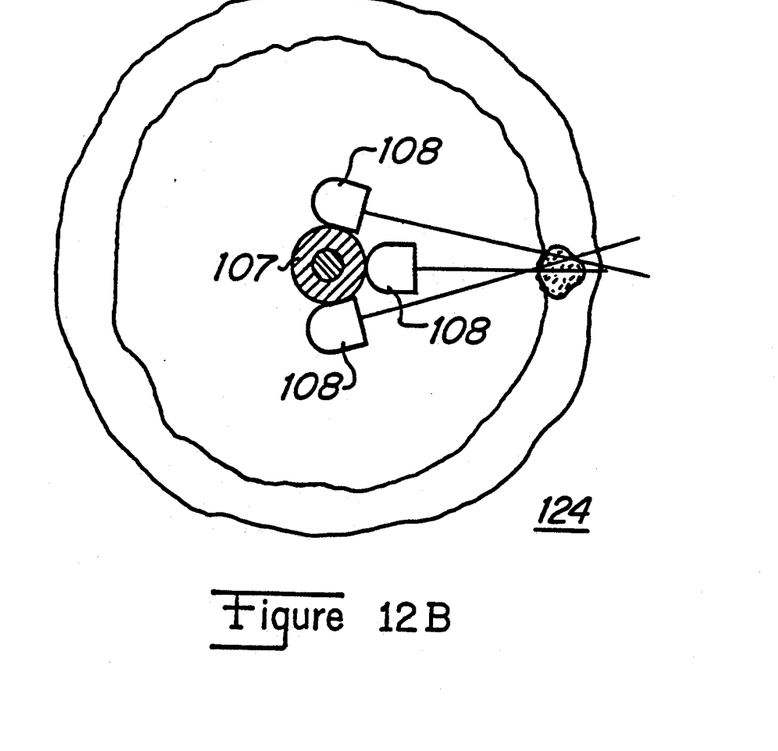
FIG. 12B shows the top view of an alternate embodiment of the invention that has three acoustic waveguides that emit acoustic signals that insonify approximately the same spot.

Surrounding fibers 108 are similar to the acoustic fiber of ultrasound probe 20 shown in FIG. 1. A combination probe could have any number of surrounding fibers 108 without departing from the scope of the invention. FIG. 11 shows the distal end of an alternate embodiment of the invention, combination probe 120, that has four surrounding fibers 108. FIGS. 12A and 12B show the distal end of other alternate embodiments, combination probe 122 and combination probe 124, that have three surrounding fibers. The proximal ends of combination probes 120, 122, and 124 are similar to that shown in FIG. 9 for combination probe 110.

In some diagnostic situations, some or all of surrounding acoustic fibers 108 may be required for acquisition of Doppler velocity information. For example, center fiber 107 aims down the longitudinal axis but the user may want to know the velocity in a branch vessel. In this case, motor 114, in FIG. 9, rotates ultrasound probe 110, at the will of the user, until it positions a surrounding acoustic fiber 108 to acquire doppler velocity information from the branch blood vessel by guiding doppler emitted acoustic signals from a piezoelectric transducer located outside the body, through blood vessels to the branch vessel and guiding some of the acoustic signals that have reflected off the red blood cells back through the blood vessels to the piezoelectric transducers. Since piezoelectric transducers 118 do not enter the body, the user can vary the frequencies of the acoustic signals separately so that each acoustic signal has the optimum frequency for the velocity of the blood that it measures.

Usually, surrounding acoustic fibers rotate continuously when imaging the body cavity. In this mode, motor 114, shown in FIG. 9, continuously rotates combination probe 110 while surrounding acoustic fibers 108 guide emitted acoustic signals from transducers 118 into the body and guide reflected acoustic signals from the body back to transducer 118. A reinforcing wire 112, which is similar to reinforcing wire 42 shown in FIG. 1, wraps around combination probe 110 and strengthens it. Transducers 118 attach to and rotate with acoustic fibers 107, 108. Electrical connections to rotating transducers 118 are made through wires 119 that attach to transducers 118 and a slip ring located on the rotating motor shaft 116.

When combination probe 110 makes doppler measurements motor 114 can rotate it because center acoustic fiber 107 does not have angular motion, and it does not have to rotate unless surrounding acoustic fiber 108 are imaging the walls of the blood vessel.

Combination probe 110 can measure the cardiac output by using center acoustic fiber 107 to measure the velocity of the blood in a vessel and using the surrounding acoustic fibers 108 to measure the cross-sectional area of the blood vessel. Multiplying these two measurements together gives the volume of blood that flows through that vessel per unit time.

FIG. 11 shows combination probe 120 that has four surrounding acoustic fibers 108 and that can measure the cardiac output. The four surrounding acoustic fibers 108 gather distance information by emitting pulses and remaining stationary until they receive reflected pulses. Then, a motor similar to motor 114 shown in FIG. 9, rotates combination probe 120 slightly, such as 5°, and surrounding fibers 108 make a new set of distance measurements. By rotating in precise discrete steps, a full 360° sector of the artery can be traced out. From this trace, the effective cross-sectional area can be calculated. The product of the cross-sectional area and the velocity measured by the Doppler probe gives the volume flow.

FIGS. 12A and 12B show an alternate embodiment of the ultrasound diagnostic probe with acoustic fibers aiming their acoustic signals in the same direction. They may insonify the same spot, as shown in FIG. 12A, with the same frequency or with different frequencies that would give different degrees of resolution. Or, they may insonify different parts of lesion. Also, each acoustic fiber may be individually disabled or the frequencies changed.

All publications and patent applications cited in this specification are herein incorporated by reference as if each publication or patent application were specifically and individually indicated to be incorporated by reference.

Although the foregoing invention has been described in some detail by way of illustration and example for purpose of clarity of understanding, it will be readily apparent to those of ordinary skill in the art and in light of the teachings of this invention, that certain changes and modifications may be made thereto without departing from the spirit or scope of the appended claims.

What is claimed is:

1. An intracavity ultrasound diagnostic probe, comprising:
   a. a means for guiding an emitted imaging acoustic signal from outside a body through a body cavity to an imaging site within the body and for guiding a reflected imaging acoustic signal from the imaging site through the body cavity to outside the body, the means for guiding has a proximal end that stays outside a body and a distal end that goes into the body;
   b. a means for rotating the means for guiding the emitted imaging acoustic signal; and
   c. a catheter covering a portion of the means for guiding that goes inside the body.

2. An apparatus, as in claim 1, wherein the means for rotating the means for guiding an acoustic signal is a motor located outside the body.

3. An apparatus, as in claim 1, further comprising a means for increasing a torsional strength of the means for guiding an acoustic signal.

4. An apparatus, as in claim 1, further comprising a means for aiming the acoustic signal at a wall of the body cavity.

5. An apparatus, as in claim 1, further comprising a means for transferring the acoustic signal from the guiding means to the imaging site with minimal loss of acoustic energy.

6. An apparatus, as in claim 5, wherein the means for transferring, further comprises an acoustic window.

7. An apparatus, as in claim 6, further comprising a means for encoding the position of the means for guiding.

8. An apparatus, as in claim 6, further comprising a lens inside the acoustic window.

9. An apparatus, as in claim 1, wherein the means for guiding is an acoustic fiber.

10. An apparatus, as in claim 9, further comprising a means for matching an acoustic impedance of the acoustic fiber with an acoustic impedance of a fluid located near a distal end port of the acoustic fiber.

11. An apparatus, as in claim 9, further comprising a wire wrapped around the acoustic fiber.

12. An apparatus, as in claim 9, further comprising an acoustic lens attached to a distal end port of an acoustic fiber.

13. An apparatus, as in claim 9, further comprising a bend in the acoustic fiber at the distal end that aims the acoustic signal.

14. An apparatus, as in claim 9, wherein the acoustic fiber has a bevelled distal end port that aims the acoustic signal.

15. An apparatus, as in claim 9, wherein an acoustic reflector located in a path of the acoustic signal aims the acoustic signal.

16. An apparatus, as in claim in the acoustic fiber is a cladded-core fiber having a cladding around a core.

17. An apparatus, as in claim 16, wherein the acoustic fiber is a cladded-core fiber having a solid cladding around a solid core.

18. An apparatus, as in claim 16, wherein the cladding is solid and the core is liquid.

19. An apparatus, as in claim 16, further comprising a section of exposed core.

20. An apparatus, as in claim 1, wherein the means for guiding an acoustic signal is a plurality of acoustic fibers.

21. An apparatus, as in claim 20, further comprising a wire wrapped around the plurality of acoustic fibers.

22. An apparatus, as in claim 20, further comprising a center acoustic fiber, located on an axis of rotation of the plurality of acoustic fibers, that guides an emitted doppler acoustic signals to the imaging site and that guides a reflected doppler signal from the imaging site and at least one surrounding acoustic fiber, located adjacent to the center acoustic fiber, each surrounding acoustic fiber guides an emitted imaging acoustic signal to the imaging site and guides the reflected imaging acoustic signal from the imaging site, each surrounding acoustic fiber has a means to aim the emitted imaging acoustic signal at the imaging site.

23. An apparatus, as in claim 20, further comprising at least two acoustic fibers, where each fiber guides an emitted imaging acoustic signal having a different frequency into approximately a same plane, the same plane is positioned normal to an axis of rotation of the acoustic fibers.

24. An apparatus, as in claim 20, further comprising at least two acoustic fibers, all fibers have a means for aiming the emitted imaging acoustic signal into adjacent planes that are positioned normal to an axis of rotation of the acoustic fibers.

25. An apparatus, as in claim 20, further comprising a look-ahead acoustic fiber, a look-to-the-side acoustic fiber, and a look-behind acoustic fiber.

26. An apparatus, as in claim 20, further comprising at least two acoustic fibers that aim the acoustic signal at a particular location in the imaging site.

27. An apparatus, as in claim 20, further comprising at least two acoustic fibers that aim the acoustic signal at a imaging site.

28. An intracavity ultrasound diagnostic probe, comprising:
 a. a means for guiding an emitted imaging acoustic signal from outside a body, through a body cavity, to an imaging site within the body, the means has a proximal end that stays outside the body and a distal end that goes into the body;
 b. a means for guiding a reflected imaging acoustic signal from the imaging site, through the body cavity, to outside the body, the guiding means has a second proximal end that stays outside the body and a second distal end for entering the body;
 c. a means for rotating the means for guiding the emitted imaging acoustic signal and the means for guiding the reflected imaging acoustic signal; and
 d. a catheter covering a portion of the means for guiding the emitted imaging acoustic signal that goes inside the body and a portion of the means for guiding the reflected imaging acoustic signal that goes inside the body.

29. An apparatus, as in claim 28, further comprising:
 e. a means for transferring the emitted acoustic signal from the guiding means to the imaging site and for transferring the reflected acoustic signal from the imaging site to the guiding means with minimal loss of acoustic energy.

30. An ultrasound diagnostic probe, as in claim 28, further comprising:
 f. a means for increasing a torsional strength of the means for guiding.

31. An ultrasound diagnostic probe, as in claim 28, further comprising:
 g. a means for aiming the emitting acoustic signal at a wall of the body cavity.

32. An ultrasound diagnostic probe, as in claim 28, wherein:
 h. the means for guiding the emitted acoustic signal further comprises at least one acoustic fiber; and
 i. the means for guiding the reflected acoustic signal further comprises at least one acoustic fiber.

33. An ultrasonic diagnostic probe, as in claim 32, wherein the acoustic fibers are cladded core fibers.

34. An ultrasonic diagnostic probe, as in claim 33, wherein the acoustic fibers are cladded-core fibers with a solid cladding around a solid core.

35. An ultrasonic diagnostic probe, as in claim 33, wherein the acoustic fibers are cladded-core fibers with a solid cladding and a liquid core.

36. An ultrasonic diagnostic probe, as in claim 32, wherein: the means for guiding the emitted acoustic signal and the means for guiding the reflected acoustic signal are combined into each acoustic fiber.

37. A method, comprising:
 a. generating an emitted imaging acoustic signal outside a body;
 b. guiding the emitted imaging acoustic signal into and through a body cavity to an imaging site that the emitted imaging acoustic signal echoes from to form a reflected imaging acoustic signal;
 c. guiding the reflected imaging acoustic signal formed at the imaging site through the body cavity to outside the body to an acoustic signal detector; and
 d. rotating the emitted imaging acoustic signal.

38. A method, as in claim 37, further comprising the steps of:
 e. aiming the emitted acoustic signal at a wall of the body cavity, 39. A method, as in claim 37, further comprising the steps of:
 f. rotating the emitted acoustic signal until the emitted acoustic signal is aimed up a branch blood vessel; and
 g. guiding the emitted acoustic signal down the branch blood vessel.

40. A method, as in claim 39, further comprising the steps of:
 h. guiding a doppler acoustic signal from outside the body to a blood vessel;
 i. guiding a reflected doppler acoustic signal from the blood vessel to outside the body;
 j. aiming the emitted imaging acoustic signal at a wall of the blood vessel;
 k. slightly rotating the emitting imaging acoustic signal a small amount after guiding the reflected acoustic signal to outside the body; and
 l. repeating the steps of aiming and slightly rotating until the emitted acoustic signals have crossed an entire cross-section of the blood vessel.

* * * * *